(12) United States Patent
Tseng et al.

(10) Patent No.: US 8,691,803 B2
(45) Date of Patent: *Apr. 8, 2014

(54) PROCESS FOR THE PREPARATION OF ANTIBIOTIC COMPOUNDS

(75) Inventors: Wei-Hong Tseng, Miaoli County (TW); Wen-Hsin Chang, Miaoli County (TW); Shiuan-Ting Chuang, Miaoli County (TW)

(73) Assignee: Savior Lifetec Corporation, Miaoli County (TW)

( * ) Notice: Subject to any disclaimer, the term of this patent is extended or adjusted under 35 U.S.C. 154(b) by 178 days.

This patent is subject to a terminal disclaimer.

(21) Appl. No.: 13/168,569

(22) Filed: Jun. 24, 2011

(65) Prior Publication Data

US 2012/0190664 A1    Jul. 26, 2012

Related U.S. Application Data

(63) Continuation-in-part of application No. 13/012,171, filed on Jan. 24, 2011, now abandoned.

(51) Int. Cl.
*A61K 31/00*     (2006.01)
*C07D 487/04*    (2006.01)

(52) U.S. Cl.
USPC ...................................... 514/210.13; 540/350

(58) Field of Classification Search
USPC ...................................... 514/210.13; 540/350
See application file for complete search history.

(56) References Cited

U.S. PATENT DOCUMENTS 5,478,820 A    12/1995  Betts et al.

FOREIGN PATENT DOCUMENTS

| WO | 01/32172 A1 | 5/2001 | |
| WO | 02/34750 | 5/2002 | |
| WO | WO 2009/150630 A2 * | 12/2009 | ............... A61K 9/00 |

* cited by examiner

*Primary Examiner* — Wu-Cheng Winston Shen
*Assistant Examiner* — Christopher R Stone
(74) *Attorney, Agent, or Firm* — WPAT, P.C.; Anthony King

(57) ABSTRACT

The present invention relates to a process for the preparation of carbapenem antibiotic compounds, which are useful for intravenous and intramuscular administration.

9 Claims, No Drawings

PROCESS FOR THE PREPARATION OF ANTIBIOTIC COMPOUNDS

CROSS REFERENCE

This is a continuation-in-part of U.S. application Ser. No. 13/012,171, filed on Jan. 24, 2011, which is incorporated herewith by reference

BACKGROUND OF THE INVENTION

1. Field of the Invention

The present invention relates to a simplified process for preparing a product of carbapenem antibiotic compounds.

2. The Prior Arts

Carbapenem is a class of β-lactam antibiotics having a broader spectrum of antibacterial activity than other β-lactam antibiotics. The formula (I) has an unusual structure of carbapenem, which renders itself strongly resistant to typical bacterial beta-lactamse enzymes. In other words, carbapenem is able to be used as the last resort for many serious bacterial infections including gram positive and negative, aerobic and anaerobic bacteria. However, unstable propriety of carbapenem brings about a problem in commercially manufacturing. As the environmental temperature goes up, accelerating dimerization and hydrolysis deteriorate the quality of carbapenem. Take ertapenem for example, it is unstable above −20° C. and must be stored at a low temperature. Therefore, several researches disclose how to achieve a stable form of carbapenem antibiotics in its formulation and manufacturing process. In particular, several processes for conversion of salt-containing carbapenem to a formulation of the compound of formula (II) have been reported.

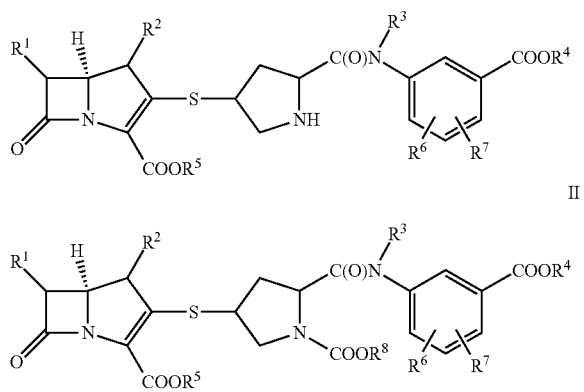

WO2001/32172 A1 describes a process with detail steps for converting ertapenem monosodium into a stable formulation. The whole process contains more than 10 steps. Even though WO2002/34750 A1 describes a similar formulation process for carbapenem antibiotics comprising the following steps of: (1) charging a solution of carbon dioxide source having a pH range of about 6.0~12.0; (2) adding an effective amount of a mole ratio of a base and active ingredient into the reaction vessel containing the solution of carbon dioxide source to maintain pH at about 6.0 to 9.0 and a temperature of about −3° C. to about 15° C.; (3) lyophilizing the solution of step (2) to yield the final formulation product of a compound of formula (I) with less than about 10% of moisture content. The actual manufacturing process of the later patent still follows more than 10 steps, including charging water for injection 3 times, weighting, carefully maintaining a pH range by alternately adding carbapenem and base.

With our continued research for developing different processes for converting carbapenem or its pharmaceutically acceptable salt, hydrate, or solvate to a final formulation product of carbapenem antibiotic with acceptable levels of degradates, solid state stability and solution stability for dosing. The process mainly simplifies the manufacturing process avoiding multiple water charging and titration, and also offers a high-quality and ready-to-use injection suitable for treatment. The other process is a crystallization directly using anti-solvent to obtain the final formulation product without lyophilizing. The present invention is able to offer a commercially viable, very low-cost, and simplified the manufacturing processes.

SUMMARY OF THE INVENTION

The objective of the present invention is to provide a simple and commercially viable process for manufacturing a stable product of carbapenem antibiotic compound of the formula (I).

Accordingly, the present invention provides an improved process for manufacturing a solution of a compound of formula (I):

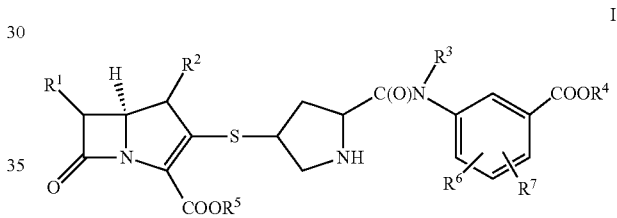

or its pharmaceutically acceptable salt, hydrate or solvate;
wherein $R^1$ is 1-hydroxyethyl, 1-fluoroethyl, or hydroxymethyl;
$R^2$ and $R^3$ are independently hydrogen, or $C_1$-$C_6$ alkyl;
$R^4$ and $R^5$ are independently hydrogen, $C_1$-$C_6$ alkyl, or alkali-metal or alkali earth-metal wherein the alkali-metal or alkali earth-metal is sodium, potassium, lithium, cesium, rubidium, barium, calcium or magnesium;
$R^6$ and $R^7$ are independently hydrogen, halo, cyano, nitro, hydroxy, carboxy, amino, $C_1$-$C_6$ alkylamino, di $C_1$-$C_6$ alkylamino, $C_1$-$C_6$ alkoxy, $C_1$-$C_6$ alkoxycarbonyl, aminosulphonyl, $C_1$-$C_6$ alkylaminosulphonyl, di-$C_1$-$C_6$ alkylaminosulphonyl, carbamoyl, $C_1$-$C_6$ alkylcarbamoyl, trifluoromethyl, sulphonic acid, sulphonic acid, $C_1$-$C_6$ alkanoylamino, $C_1$-$C_6$ alkanoyl(N—($C_1$-$C_6$)-alkyl)amino, $C_1$-$C_6$ alkanesulphonamido, $C_1$-$C_6$ alkyl-S(O)$_n$ wherein n is 0-2;
comprising the steps of:
(a) dissolving a carbonate source and a base in a diluent to form a first solution at a temperature from 0° C. to 25° C., wherein a mole ratio of the carbonate source to the compound of formula I is 0.5 to 1.5, and a mole ratio of the base to the compound of formula I is 0 to 1.0; and
(b) mixing the compound of formula I with the first solution at a temperature from −5° C. to 25° C. to form the solution.

The process optimizes a process by the following modification: reducing over 10-step manufacturing, simplifying multiple titrations and loosing up the in-process restrictions. The pH naturally falls at the appropriate range from about 6.5 to about 8.5 without titration when the molar ratio of the base to the compound of formula I is 0.7 to 1.0 in step (a). In other embodiment, the molar ratio of the base to the compound of formula I is larger than 0.1 and less than 0.7 in step (b), the process just need to add a portion of the base once to maintain pH. The solution is able to be a high-quality and ready-to-use injection suitable for treatment. After lyophilizing the solution, the stable product is able to transport at a temperature below 25° C. As injections, the stable products dissolving in appropriate diluents are able to be used in treatment.

The other objective of the present invention is to provide a very low-cost, simple and commercially viable crystallizing process for directly converting a solution of a compound of formula (I) with pH 6.5~8.5 to a stable product of the formula (II) or its pharmaceutically acceptable salt, hydrate or solvate by using an organic solvent without lyophilizing.

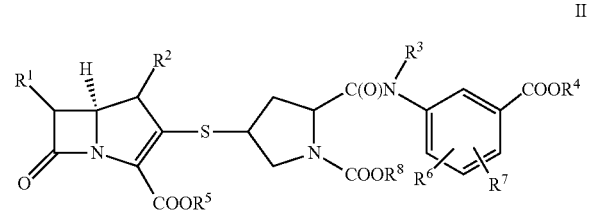

wherein $R^1 \sim R^7$ are as defined as defined in paragraph 6; $R^8$ is independently hydrogen, $C_1$-$C_6$ alkyl, or alkali-metal or alkali earth-metal wherein the alkali-metal or alkali earth-metal is sodium, potassium, lithium, cesium, rubidium, barium, calcium or magnesium.

DETAILED DESCRIPTION OF THE PREFERRED EMBODIMENT

As used herein, the term "hydrate" is used in the conventional sense to include the compounds of formula I and Ia in physical association with water.

As used herein, the term "one mole equivalent" is defined as one mole of carbon dioxide or base source per one mole of active carbapenem (or active drug).

As used herein, the term "active carbapenem" refers to the actual amount of beta-lactam, unstablilized and stabilize carbapenem, and/or alkali-metal salt or alkali earth-metal salt containing carbapenem.

The present invention relates to pharmaceutical compositions which contain the compound of formula I as well as salts, stable forms and hydrates thereof. Compound of formula I is a carbapenem antibiotic that is particularly useful for intravenous and intramuscular administration.

The process of the present invention generally uses a carbon dioxide source. Preferred sources of carbon dioxide are carbon dioxide (gas, liquid or solid), carbonates and bicarbonates, and more preferably sodium carbonate and sodium bicarbonate, which can be incorporated in the solution, such that an appropriate pH, e.g., about 6.5-8.5, is obtained upon dissolution. The native pH of the monosodium salt of compound I is approximately 5~6.

Compounds of formula I can be synthesized in accordance with U.S. Pat. No. 5,478,820 issued to Betts et al. on Dec. 26, 1995, the teachings of which are incorporated herein by reference.

Generally stable product of formula I can be produced by lyophilizing a reconstituted solution blending the compound of formula (I), a carbonate source, and a base. In many instances it is preferred to dissolve the compound of formula I with the carbonate source such as sodium bicarbonate and the base such as sodium hydroxide, in diluents, and then to lyophilize the resulting composition, thus providing a powder composition containing a compound of formula II, or a pharmaceutically acceptable salt, or hydrate thereof.

The carbonate source in gas, solid, liquid or aqueous form of the present invention is selected from the group consisting of carbon dioxide, sodium bicarbonate, potassium bicarbonate, sodium carbonate, potassium carbonate, calcium carbonate, cesium carbonate, magnesium carbonate, lithium carbonate, and a mixture thereof.

The base in solid, liquid or aqueous form of the present invention is selected from the group consisting of sodium hydroxide, lithium hydroxide, potassium hydroxide, calcium hydroxide, barium hydroxide, magnesium hydroxide, lithium methoxide, sodium ethoxide, potassium ethoxide, lithium tert-butoxide, sodium tert-butoxide and potassium tert-butoxide.

The diluent of the present invention is selected from the group consisting of water for injection, sodium chloride injection, bacteriostatic water for injection, and lidocaine HCl injection.

The present invention optimizes a solution process by the following modification: reducing over 10-step manufacturing, simplifying multiple titrations and loosing up the in-process restrictions. The novel process is able to provide better quality of stable formulation of carbapenem antibiotics or the same quality (above 94% purity analyzed by HPLC) as quality of other competitors' product (about 94%, purchased from Merck), comprising the steps of:

(a) dissolving a carbonate source and a base in a diluent to form a first solution at a temperature from 0° C. to 25° C., wherein a mole ratio of the carbonate source to the compound of formula I is 0.5 to 1.5, and a mole ratio of the base to the compound of formula I is 0 to 1.0; and (b) mixing the compound of formula I with the first solution at a temperature from −5° C. to 25° C. to form the solution.

Finally, the solution is able to be a high-quality and ready-to-use injection suitable for treatment. After lyophilizing the solution, or after crystallizing by mixing the solution with an organic anti-solvent, the stable product is suitable for treatment of bacterial infections after diluting with appropriate diluents.

The process not only simplifies steps of manufacturing and relaxes the restrictions on the manufacturing but also maintains high quality of final products. When the molar ratio of the base to the compound of formula I is 0.7 to 1.0 in step (a), a temperature range of step (a) is from about 0° C. to 25° C., preferably from 0° C. to 15° C. And the pH naturally falls at the appropriate range from about 6.5 to about 8.5 without making actions to maintain pH. The whole process is just simply adding, dissolving, mixing and lyophilizing. In the other embodiment, the molar ratio of the base to the compound of formula I is larger than 0.1 and less than 0.7 in step (a), the simplified process is also able to maintain high quality of final products. And a portion of the base is charged to maintain the pH in the step (b) at a temperature range from about −5° C. to 25° C., preferably from −5° C. to 15° C. The whole process just has to maintain pH with a portion of the base once. The solution is then lyophilized to obtain the powdered stable product.

The other process for manufacturing a stable compound of formula II can provide high-quality powdered product by crystallizing without lyophilizing. By skipping lyophilizing, advantages of the process are as following: very low cost, high quality product with normally above 96% purity analyzed by HPLC, and room-temperature (≤25° C.) store available. When the mole ratio of the base to the compound of formula I is 0 to 0.7 in step (a), a portion of the base was added into the solution of the compound of formula I to maintain pH at 6.5 to 8.5. Then the solution is charged into an organic anti-solvent under stirring to crystallize a compound of formula II or its pharmaceutically acceptable salt, hydrate or solvate.

The organic anti-solvent is selected from the group consisting of methanol, ethanol, 1-propanol, isopropyl alcohol, 1-butanol, sec-butanol, methyl acetate, methyl ethyl ketone, tetrahydrofuran (THF), isopropylamine (IPA), maleic anhydride, ether, ethyl acetate (EA), isopropyl acetate(IPAc), (di) isopropyl ether (IPE), methyl t-butyl ether (MTBE) and a mixture thereof.

Consequently, the compound of formula II is filtered and dried to get a stable product with less than about 10% moisture content. Thus, the powdered, stable and high-quality compound of formula II can be obtained without lyophilizing by means of low-cost crystallizing process.

Special preference is given to the compound (Ia) mentioned in the examples, especially each individual compound.

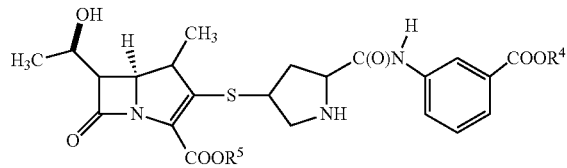

Ia or its pharmaceutically acceptable salt, hydrate or solvate wherein $R^4$ and $R^5$ are independently hydrogen, or $C_1$-$C_6$ alkyl, or alkali-metal or alkali earth-metal wherein the alkali-metal or alkali earth-metal is sodium, potassium, lithium, cesium, rubidium, barium, calcium or magnesium.

The present relates especially to the manufacturing steps mentioned in the following examples. Although the present invention has been described with reference to the preferred embodiments thereof, it is apparent to those skilled in the art that a variety of modifications and changes may be made without departing from the scope of the present invention which is intended to be defined by the appended claims.

Example 1

Sodium bicarbonate 1.25 g, 1.0 mole equivalent of sodium bicarbonate/active carbapenem, was added to a reactor already containing 25 ml of water for injection. A sufficient amount of sodium hydroxide, 0.73 mole equivalent of sodium bicarbonate/active carbapenem, was then dissolved thoroughly into the reactor. The solution had a pH range between 10 and 11, and the solution was held at a temperature of from 0° C. to 5° C. Unstable carbapenem 7.56 g of free acid was gradually added to the solution about 30 minutes to ensure complete dissolution, and the solution had a pH at about 8.0.

While maintaining the solution at a temperate between −5° C. and 5° C., the solution was filtered utilizing a filter containing a 0.22 mm filter to form a sterile solution. Then, the sterile solution was frozen to −40° C. and placed onto the shelves of lyophilizer. Thereafter, the lyophilizer was then operated according to the following cycle:
1. soak at −40° C. shelf temperature for 2 hrs;
2. heat to −20° C. shelf temperature in 40 mins;
3. hold shelf temperature at −20° C. and below 80 mTorr pressure for 24~48 hrs;
4. heat to 10° C. shelf temperature in 5 hrs;
5. heat to 40° C. shelf temperature in 40 mins;
6. hold at 40° C. and below 80 mTorr for 3 hrs;
7. heat to 60° C. shelf temperature in 40 mins;
8. hold at 60° C. and below 80 mTorr for 3 hrs;
9. cool to the shelves to ambient temperature (20° C.~30° C.);

Finally, the final formulation product exhibited a white-powder form and a moisture content of 5%. Table 1 provides the High Performance Liquid Chromatography (HPLC) results in area % of in process samples collected during the formulating of carbapenem antibiotic for this example.

TABLE 1

| HPLC, Area % | Carbapenem | Total degradates | Total dimers | Ring open |
|---|---|---|---|---|
| Bulk drug | 98.94% | 1.06% | 0.27% | 0.24% |
| Prefilter solution | 98.37% | 1.63% | 0.37% | 0.69% |
| Lyophilized product | 95.38% | 4.62% | 1.29% | 2.14% |

Example 2

The method of Example 2 according to Example 1 to describe the mole ratio of base to the compound of formula I is 0.1 to 0.7 in step (a), and the final solution maintains pH at 6.5 to 8.5.

Sodium bicarbonate 0.98 g, 1.0 mole equivalent of sodium bicarbonate/active carbapenem, was added to a reactor containing 18 ml of water for injection. A sufficient amount of sodium hydroxide, 0.1 mole equivalent of sodium bicarbonate/active carbapenem, was then dissolved thoroughly into the reactor. The solution had a pH at about 9, and then the solution was held at a temperature of from 0° C. to 5° C. Unstable carbapenem 5.8 g of free acid was gradually added to the solution about 30 minutes; at the mean time, a portion of sodium hydroxide were added to achieve 0.73 mole ratio of sodium hydroxide to active carbapenem (appropriate range between 0.7 and 1.0). The final pH was at about 7.7 (appropriate range between about 7.0 and about 8.0).

The solution was filtered utilizing a filter containing a 0.22 mm filter at a temperate of from −5° C. to 5° C. The solution was frozen to −40° C. and placed onto the shelves of Lyophilizer. Thereafter, the lyophilizer was operated according to the same cycle described in Example 1. Table 2 illustrates the High Performance Liquid Chromatography (HPLC) results in area % of in process samples collected during the formulating of carbapenem antibiotic for Example 2.

TABLE 2

| HPLC, Area % | Carbapenem | Total degradates | Total dimers | Ring open |
|---|---|---|---|---|
| Bulk drug | 98.82% | 1.18% | 0.42% | 0.23% |
| Prefilter soln. | 98.08% | 1.92% | 0.70% | 0.59% |
| Lyophilized product | 96.03% | 3.97% | 1.01% | 1.83% |

Example 3

The general procedure described in Example 2 was utilized to prepare the formulation of this example. The total mole ratio of sodium hydroxide to active carbapenem achieve to 0.76 (appropriate range from 0.7 to 1.0). The individual amount of reagents is listed in Table 3.

TABLE 3

| Carbapenem | Water for Injection | NaHCO$_3$(s) | NaOH |
|---|---|---|---|
| 7.94 g | 25 ml | 1.0 mole equivalent | 0.76 mole equivalent |

Table 4 illustrates the High Performance Liquid Chromatography (HPLC) results in area % of in process samples collected during the formulating of carbapenem antibiotic for Example 3.

TABLE 4

| HPLC, Area % | Carbapenem | Total degradates | Total dimers | Ring open |
|---|---|---|---|---|
| Bulk drug | 98.75% | 1.25% | 0.35% | 0.20% |
| Prefilter solution | 98.13% | 1.87% | 0.67% | 0.51% |
| Lyophilized product | 97.24% | 2.76% | 1.1% | 0.86% |

Example 4

At a temperature below 25° C., one mole equivalent of sterile sodium bicarbonate and 0.7 mole equivalent of sterile sodium hydroxide were added into a container. The container was then charged 10 ml of water for injection (WFI), shook thoroughly to form a clear solution within 5 minutes. The pH of the solution is naturally at 6.5 to 8.5. After mixing with one mole equivalent of sterile carbapenem sodium, a high-quality and ready-to-use solution suitable for treatment was formed.

Table 5 illustrates the High Performance Liquid Chromatography (HPLC) results in area % and show the stability of the reconstituted solution produced by the above processes. Purity of the reconstituted solution, above 97%, is 3% higher than commercial products of other competitors. Also, the reconstituted solution exhibits good stability either at a temperature of from about 0° C. to 5° C. or at a temperature of from about 25° C. to 30° C. as shown in Table 5.

TABLE 5

| Purity (area %) | | Temp | |
|---|---|---|---|
| | | 0-5° C. | 25-30° C. |
| Time | 0 h | 98.24% | 97.42% |
| | 1.5 h | NA | 96.22% |
| | 3 h | 97.42% | 94.51% |
| | 4 h | 97.05% | NA |

General Procedure for Preparing a Stable Carbapenem of Formula II by Crystallizing Examples 5~25

The procedure contains three sections, including pre-preparation of carbapenem solution, pre-preparation of anti-solvent and crystallization. Carbapenem solution was prepared by the following steps:

(1) A sufficient amount of sodium carbonate was dissolved in water to form a solution, and sodium hydroxide solution was optionally added into the first solution at a temperature from 0° C. to 10° C., wherein a mole ratio of the carbonate source to the compound of formula I was 0.9 to 1.3, and a mole ratio of the base to the compound of formula I was 0 to 0.7.

(2) An ertarpenem compound of formula I was mixed with the first solution at a temperature from 0° C. to 10° C., and the pH was maintained at 6.5-8.5 with sodium hydroxide solution.

Organic anti-solvent was prepared by 0.22 μm filtering and pre-cooling. The organic anti-solvent is able to be selected from the group consisting of methanol, ethanol, 1-propanol, isopropyl alcohol, 1-butanol, sec-butanol, methyl acetate, methyl ethyl ketone, tetrahydrofuran (THF), isopropylamine (IPA), maleic anhydride, ether, ethyl acetate(EA), isopropyl acetate (IPAc), (di)isopropyl ether (IPE), methyl t-butyl ether (MTBE) and a mixture thereof.

The pre-preparing carbapenem solution was added into the pre-cooled organic anti-solvent under stirring at 0~10° C., and carbapenem of formula II crystallized to form a suspension solution. The total volume of the anti-solvent was usually 15~40 times the carbapenem solution represented 15~40P. After completion of charging of carbapenem solution, the mixing solution kept stirring the solution about 0.5~2 hours at 0~5° C. Then, the suspension with precipitation was filtered at a temperature range from −10 to 30° C., and optionally treated with alcohol/ether or ketone mixture and dried to amorphous form of carbapenem of stable formula II. Generally, using 15~20P IPA, 25~35P IPA/THF/MeOH mixtures, 20~25P IPA/IPAc mixtures in the ratio 10:1 to 5:1, IPA/MeOH mixtures in the ratio 2:1 to 8:1, MeOH/MA or EtOH/MA mixtures in the ratio 1:2 to 1:3 20~30P MeOH/MA/IPA or EtOH/MA/IPA mixtures in the ratio 1:2:2 to 1:3:3 as anti-solvent to crystallize the final product of carbapenem of stable formula II from carbapenem solution has about 95~98%, 70~80%, 90~96%, 70~90%, 92~98%, 94~98% yield performance (see Table 8).

Example 5

Preparation of Carbapenem Solution with Base in a First Stage

Sodium bicarbonate 0.505 g, 1.2 mole equivalent of carbapenem, and sodium hydroxide, 0.1 mole equivalent of carbapenem was added to a reactor already containing 20 ml of cold water at 0-10° C. A sufficient amount of carbapenem of formula I was charged into the reactor, and the pH of the solution was maintain at a range from 7.5 to 8.3 with a sufficient amount of sodium hydroxide to ensure complete dissolution at a temperature of from 0° C. to 5° C. for about 1 hour. The total mole equivalent of sodium hydroxide used to maintain pH was 0.80. Then, the solution was at a pH 7.88 and filtered at 0~5° C. using a 0.22 μm filter to obtain sterile solution applied to further crystallization process.

Preparation of Anti-Solvent:

500 ml IPA was filtered using a 0.22 μm filter into a sterile container, mixed and cooled to −5~0° C. under the nitrogen.

Crystallization:

Carbapenem solution was added into the pre-cooled anti-solvent under stirring at −5~0° C., and carbapenem of formula II crystallized to form a suspension solution. The total volume of the anti-solvent was a times the carbapenem solution usually represented 15P. After completion of charging of carbapenem solution, the mixing solution kept stirring the solution about 0.5 hour at −5~0° C. Then, the suspension with precipitation was filtered under N$_2$(g) purging at −5~0° C. and dried to yield of amorphous form of carbapenem of stable formula II.

Example 6

Preparation of Carbapenem Solution with Base in a Latter Stage

Sodium bicarbonate 1.77 g, 1.0 mole equivalent of carbapenem, was added slowly to a reactor already containing 30 ml of cold water at 0-10° C. A sufficient amount of carbapenem of formula I was charged into the reactor, and the pH of the solution was maintain at a range from 7.0 to 8.0 with a sufficient amount of sodium hydroxide to ensure complete dissolution at a temperature of from 0° C. to 5° C. for about 1 hour. The total mole equivalent of sodium hydroxide used to maintain pH was 0.83. Then, the solution was at a pH 7.58 and filtered at −2~5° C. using a 0.22 μm filter to obtain 51.5 ml of sterile solution. 15 ml of the solution was applied to further crystallization process.

Preparation of Anti-Solvent:

MeOH and THF were filtered using a 0.22 μm filter into a sterile container, mixed and cooled to 0~5° C. under the nitrogen. The mixing organic solvent (used as anti-solvent) contained 125 ml of MeOH and 250 ml THF.

Crystallization:

15 ml carbapenem solution was added into the pre-cooled anti-solvent under stirring at 0-5° C., and carbapenem of formula II crystallized to form a suspension solution. The total volume of the anti-solvent was 25 times the carbapenem solution usually represented 25P. After completion of charging of carbapenem solution, the mixing solution kept stirring the solution about 1~1.5 hours at 0~5° C. Then, the suspension with precipitation was filtered under $N_2(g)$ purging at room temperature and dried to yield 2.88 g of amorphous form of carbapenem of stable formula II. The yield of example 5 was 74.1%, and the analysis result was provided in Table 8.

Example 7 to Example 20

The procedure of these examples is similar to the procedure of Example 6 except that the crystallizing process has small differences in examples 7~20, such as organic anti-solvent, the volume of the organic anti-solvent, the pre-cooling temperature, the temperature of crystallization and the crystallization time. These different parameters and analysis results are listed in Tables 6, 7 and 8.

In viewing of Table 8 and Table 9 (Results of Comparative Example), it reveals some advantages of the invention. First, the yield of the method via crystallization is not only able to reach above 95% but also comparable to that of lyophilization or that of WO2002/34750 (yield: 93~98%). Second, because of avoiding decaying hazards from lyophilizing, the purity of the method via crystallization is higher than that of the method via lyophilization or WO2002/34750.

TABLE 6

Using other solvent as anti-solvent

| | Examples | | | |
|---|---|---|---|---|
| | Example-7 | Example-8 | Example-9 | Example-10 |
| Anti-solvent | 1-PrOH | 1-PrOH/MeOH/MA | MeOH/MEK | 2-BuOH |
| Volume of anti-solvent | 33P | 9P/9P/13P | 10P/20P | 33P |
| pre-cooling/Crystallization Temperature | | 0-5° C. | | |
| Crystallization Time | | 0.5~1 h | | |
| Product | | Dry powder | | A few Sticky precipitates |

**MA: methyl acetate; MEK: methyl ethyl ketone

TABLE 7

Using IPA (isopropyl alcohol) as anti-solvent

| | Examples | | | |
|---|---|---|---|---|
| | Example-11 | Example-12 | Example-13 | Example-14 |
| Anti-solvent | IPA | IPA | IPA | IPA |
| Volume of anti-solvent | 25P | 25P | 20P | 20P |
| pre-cooling Temperature | 0~5° C. | −10~−5° C. | 0~5° C. | 0~5° C. |
| Crystallization Temperature | 0~5° C. | −5~−15° C. | 0~5° C. | −10~−15° C. |
| Crystallization Time | 2 h | 0.5~2 h | 1.5 h~2 h | 1.5 h~2 h |
| Product | Dry powder | Dry powder | Dry powder | Dry powder |
| Yield | 90.0% | 85.0% | 97.3% | 98.31% |

TABLE 8

Analysis results of the product of formula II

| Example | Organic solvent | Yield (%) | Purity (%) by HPLC | Carbapenem | Dimers | Ring-Opened |
|---|---|---|---|---|---|---|
| 6 | IPA | 74.1 | Prefilter solution | 97.9 | 0.62 | 0.67 |
| | | | Stable product | 97.0 | 0.88 | 1.16 |
| 11 | IPA | 90.0 | Prefilter solution | 98.7 | 0.40 | 0.45 |
| | | | Stable product | 97.3 | 0.56 | 1.24 |

TABLE 8-continued

Analysis results of the product of formula II

| Example | Organic solvent | Yield (%) | Purity (%) by HPLC | | Carbapenem | Dimers | Ring-Opened |
|---|---|---|---|---|---|---|---|
| 12 | IPA | 85.0 | Prefiliter solution | | 98.7 | 0.40 | 0.45 |
|  |  |  | Stable product | | 97.4 | 0.61 | 1.13 |
| 13 | IPA | 97.3 | Prefiliter solution | | 97.8 | 0.61 | 0.67 |
|  |  |  | Stable product | | 97.4 | 0.64 | 1.05 |
| 14 | IPA | 98.3 | Prefiliter solution | | 97.8 | 0.61 | 0.67 |
|  |  |  | Stable product | | 97.3 | 0.70 | 1.00 |
| 15 | IPA/MeOH | 87.7 | Prefiliter solution | | 98.0 | 0.5 | 0.7 |
|  |  |  | Stable product | | 97.2 | 0.6 | 1.2 |
| 16 | IPA/MeOH/THF | 74.7 | Prefiliter solution | | 97.9 | 0.7 | 0.6 |
|  |  |  | Stable product | | 96.6 | 0.9 | 1.5 |
| 17 | MA/MeOH | 92.8 | Prefiliter solution | | 96.8 | 1.4 | 0.9 |
|  |  |  | Stable product | | 95.8 | 1.1 | 1.9 |
| 18 | IPA/MeOH/MA | 96.1 | Prefiliter solution | | 97.9 | 0.8 | 0.5 |
|  |  |  | Stable product | | 96.5 | 1.3 | 1.3 |
| 19 | IPA/IPAc | 92.4 | Prefiliter solution | | 97.5 | 0.9 | 0.8 |
|  |  |  | Stable product | | 95.1 | 0.9 | 3.0 |
| 20 | MA/EtOH | 96.3 | Prefiliter solution | | 96.84 | 0.9 | 1.0 |
|  |  |  | Stable product | | 95.8 | 1.1 | 1.5 |

TABLE 9

Results of Comparative Example

| Comparative Example | Purity (%) by HPLC | Carbapenem | Dimers | Ring-Opened |
|---|---|---|---|---|
| 1 | Prefiliter solution | 97.6 | 1.1 | 1.0 |
|  | Lyophilized product | 95.6 | 1.6 | 2.5 |
| 2 | Prefiliter solution | 98.0 | 0.9 | 0.9 |
|  | Lyophilized product | 95.9 | 1.5 | 2.3 |
| 3 | Prefiliter solution | 97.6 | 1.0 | 1.2 |
|  | Lyophilized product | 94.7 | 2.3 | 2.7 |

Comparative Example 1 to Comparative Example 3 illustrate the synthesis of compound of formula II, which was carried out following the method given by WO2002/34750.

Comparative Example 1

28 g of sodium bicarbonate were dissolved into a compounder with pre-cooled (about 5° C.) 400 ml of Water for injection (WFI), and the sodium bicarbonate solution was held at 1~5° C. and pH 8.1~8.5. Unstable carbapenem 160 g of free acid were divided into ten equal portions and added to the sodium bicarbonate solution along with 2N sodium hydroxide solution to form a mixing solution for around 1 hour. The solution was held at 1~6° C. and the pH at about 7.8 by charging 2N sodium hydroxide solution. After finishing the addition of carbapenem, the weight of the solution was adjusted to 834.6 g with WFI at −1~5° C. with additional agitation for 20 minutes. Then, the weight of the solution was adjusted to 888.0 g with chilled WFI at −1~5° C. with further agitation for 5 minutes. The mole equivalent of sodium bicarbanate to carbapenem of free acid is 1.0. The mole equivalent of sodium hydroxide to carbapenem of free acid is 0.93.

The solution was then filtered using a sterile 0.22 μm filter into a sterile container at −1~5° C. Immediately thereafter, about 6.33 g of the sterile solution was placed into 20 ml vials and frozen to about −70° C. The vials were placed into a Virtis Lyophilizer pre-cooled to about −40° C., and the lyophilizer was the operated as the following cycle:
(1) soak at −40° C. shelf temperature for 2 hrs;
(2) heat to −20° C. shelf temperature in 40 mins;
(3) hold shelf temperature at −20° C. and below 80 mTorr pressure for about 48 hrs;
(4) heat to 10° C. shelf temperature in 5 hrs;
(5) heat to 40° C. shelf temperature in 40 mins;
(6) hold at 40° C. and below 80 mTorr for 3 hrs;
(7) heat to 60° C. shelf temperature in 40 mins;
(8) hold at 60° C. and below 80 mTorr for 3 hrs;
(9) cool to the shelves to ambient temperature (20° C.~30° C.);
(10) stopper under partial vacuum of about 0.9 bar/700 torr.
Finally, the powdered carbapenem compound of formula II was form in the vials after lyophilizing. The analysis result of the final formulation product is provided in Table 10.

Comparative Example 2 to Comparative Example 3

The procedure of these examples are similar to the procedure of Comparative Example 1 except that the mole equivalent of the sodium hydroxide to carbapenem in Comparative Example 2 is 0.83, and the mole equivalent of the sodium hydroxide to carbapenem in Comparative Example 3 is 0.85. The analysis results of these examples of the final formulation product were provided in Table 10.

A number of embodiments of the invention have been described. Nevertheless, it will be understood that various modifications may be made without departing from the spirit and scope of the invention. Accordingly, other embodiments are within the scope of the following claims.

What is claimed is:
1. A process for manufacturing a compound of formula II,

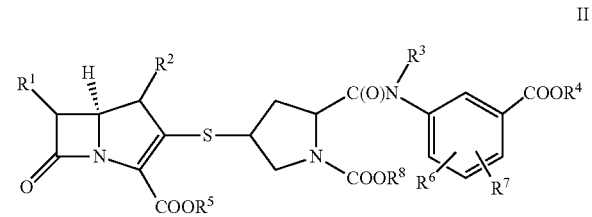

II or its pharmaceutically acceptable salt, hydrate or solvate without lyophilizing;
wherein,
$R^1$ is 1-hydroxyethyl, 1-fluoroethyl, or hydroxymethyl;

$R^2$ and $R^3$ are independently hydrogen, or $C_1$-$C_6$ alkyl;

$R^4$ and $R^5$ are independently hydrogen, $C_1$-$C_6$ alkyl, or alkali-metal or alkali earth-metal wherein the alkali-metal or alkali earth-metal is sodium, potassium, lithium, cesium, rubidium, barium, calcium or magnesium;

$R^6$ and $R^7$ are independently hydrogen, halo, cyano, nitro, hydroxy, carboxy, amino, $C_1$-$C_6$ alkylamino, di $C_1$-$C_6$ alkylamino, $C_1$-$C_6$ alkoxy, $C_1$-$C_6$ alkoxycarbonyl, amino sulphonyl, $C_1$-$C_6$ alkylaminosulphonyl, di-$C_1$-$C_6$ alkylaminosulphonyl, carbamoyl, $C_1$-$C_6$ alkylcarbamoyl, trifluoromethyl, sulphonic acid, $C_1$-$C_6$ alkanoylamino, $C_1$-$C_6$ alkanoyl(N—($C_1$-$C_6$)-alkyl)amino, $C_1$-$C_6$ alkanesulphonamido, $C_1$-$C_6$ alkyl-S(O)$_n$ wherein n is 0-2; and $R^8$ is hydrogen, sodium, potassium, lithium, cesium, barium, rubidium, calcium or magnesium;

consisting of:

(a) dissolving a carbonate source and a base in a diluent to form a first solution at a temperature from 0° C. to 25° C., wherein a mole ratio of the carbonate source to a compound of formula I is 0.5 to 1.5, and a mole ratio of the base to the compound of formula I is 0 to 0.7;

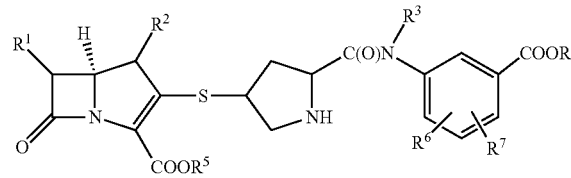

I

Or its pharmaceutically acceptable salt, hydrate or solvate, wherein $R^1$, $R^2$, $R^3$, $R^4$, $R^5$, $R^6$ and $R^7$ are defined as the compound of formula II;

(b) mixing the compound of formula I with the first solution at a temperature from −5° C. to 25° C. to form a solution of the compound of formula I, a portion of the base was added into the solution of the compound of formula I to maintain pH at 6.5 to 8.5; and (c) mixing the solution of the compound of formula I with an organic anti-solvent under stirring to crystallize a compound of formula II or its pharmaceutically acceptable salt, hydrate or solvate, wherein the total volume of the organic anti-solvent is 15 to 40 times the solution of the compound of formula I, and the organic anti-solvent is selected from the group consisting of methanol, ethanol, 1-propanol, isopropyl alcohol, 1-butanol, sec-butanol, methyl acetate, methyl ethyl ketone, tetrahydrofuran (THF), isopropylamine (IPA), maleic anhydride, ether, ethyl acetate (EA), isopropyl acetate (IPAc), (di) isopropyl ether (IPE), methyl t-butyl ether (MTBE) and a mixture thereof.

2. The process of claim 1, wherein the carbonate source in gas, solid, liquid or aqueous form is selected from the group consisting of carbon dioxide, sodium bicarbonate, potassium bicarbonate, sodium carbonate, potassium carbonate, calcium carbonate, cesium carbonate, magnesium carbonate, lithium carbonate, and a mixture thereof.

3. The process of claim 1, wherein the base, solid, liquid or aqueous form is selected from the group consisting of sodium hydroxide, lithium hydroxide, potassium hydroxide, calcium hydroxide, barium hydroxide, magnesium hydroxide, lithium methoxide, sodium ethoxide, potassium ethoxide, lithium tert-butoxide, sodium tert-butoxide and potassium tert-butoxide, and a mixture thereof.

4. The process of claim 1, wherein the diluent is selected from the group consisting of water for injection, sodium chloride injection, bacteriostatic water for injection, and lidocaine HCl injection.

5. The process of claim 1, wherein the temperature of the step (a) is preferably from about 0° C. to 15° C.

6. The process of claim 1, wherein the temperature of the step (b) is preferably from about −5° C. to 15° C.

7. The process of claim 1, wherein the compound of formula I is represented by formula Ia

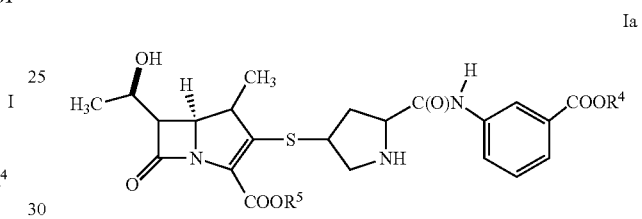

Ia or its pharmaceutically acceptable salt, hydrate or solvate wherein, $R^4$ and $R^5$ are independently hydrogen, or alkali-metal or alkali earth-metal wherein the alkali-metal or alkali earth-metal is sodium, potassium, lithium, cesium, barium, rubidium, calcium or magnesium.

8. The process of claim 1, wherein the compound of formula II is then filtered and dried to get a stable product with less than about 10% moisture content.

9. The process of claim 8, wherein the compound of formula II is represented by formula IIa:

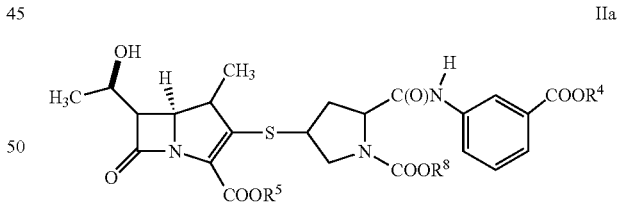

IIa or its pharmaceutically acceptable salt, hydrate or solvate wherein, $R^4$, $R^5$ and $R^8$ are independently hydrogen, sodium, potassium, lithium, cesium, barium, rubidium, calcium or magnesium.

\* \* \* \* \*